(12) United States Patent
Kawamura et al.

(10) Patent No.: US 7,321,066 B2
(45) Date of Patent: Jan. 22, 2008

(54) METHOD FOR PRODUCING AROMATIC DIAMINE DERIVATIVE

(75) Inventors: Hisayuki Kawamura, Chiba (JP); Hiroyuki Matsui, Saitama (JP); Koji Hirota, Saitama (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 234 days.

(21) Appl. No.: 10/544,764

(22) PCT Filed: Jan. 28, 2004

(86) PCT No.: PCT/JP2004/000774

§ 371 (c)(1),
(2), (4) Date: Aug. 8, 2005

(87) PCT Pub. No.: WO2004/069785

PCT Pub. Date: Aug. 19, 2004

(65) Prior Publication Data

US 2006/0063952 A1    Mar. 23, 2006

(30) Foreign Application Priority Data

Feb. 10, 2003  (JP) .............................. 2003-032052

(51) Int. Cl.
*C07C 209/00* (2006.01)
*C07C 209/12* (2006.01)
(52) U.S. Cl. ...................... 564/385; 564/385; 564/407
(58) Field of Classification Search ................ 564/385, 564/407
See application file for complete search history.

(56) References Cited

U.S. PATENT DOCUMENTS

| | | | | |
|---|---|---|---|---|
| 5,648,539 A | * | 7/1997 | Goodbrand | ................. 564/309 |
| 5,648,542 A | * | 7/1997 | Goodbrand et al. | ......... 564/405 |
| 5,929,281 A | * | 7/1999 | Nishiyama et al. | ......... 564/386 |

FOREIGN PATENT DOCUMENTS

| | | |
|---|---|---|
| DE | 36 20 639 | 12/1987 |
| EP | 1 018 505 | 7/2000 |

\* cited by examiner

*Primary Examiner*—Yvonne Eyler
*Assistant Examiner*—Yate' K Cutliff
(74) *Attorney, Agent, or Firm*—Steptoe & Johnson LLP

(57) ABSTRACT

The invention provides a method for efficiently producing an aromatic diamine derivative represented by formula (3) at high yield, the method including reacting an aromatic amide represented by formula (1) with an aromatic halide represented by formula (2):

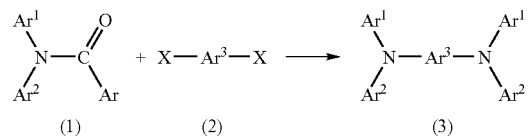

(wherein each of Ar, $Ar^1$ and $Ar^2$ represents a substituted or unsubstituted aryl group or heteroaryl group; $Ar^3$ represents a substituted or unsubstituted arylene group or heteroarylene group; and X represents a halogen atom).

9 Claims, No Drawings

METHOD FOR PRODUCING AROMATIC DIAMINE DERIVATIVE

CLAIM OF PRIORITY

This application claims priority under 35 U.S.C. § 371 of International Application No. PCT/JP2004/000774, filed Jan. 28, 2004, which claims priority of Japanese Patent Application No. 2003-032052, filed Feb. 10, 2003.

TECHNICAL FIELD

The present invention relates to a novel method for producing an aromatic diamine derivative; and more particularly to a method for producing an aromatic diamine derivative which is applied as a charge transport material of an electrophotographic photoconductor or as an organic electroluminescent device material.

BACKGROUND ART

Aromatic diamine compounds have been applied as a charge transport material of an electrophotographic photoconductor or as an organic electroluminescent (EL) device material. Particularly in the case where an aromatic diamine compound is applied as an organic EL device material, when the device material does not have a high glass transition temperature, the resultant organic EL device fails to exhibit heat resistance. Therefore, many attempts have been made to develop an aromatic diamine derivative containing in the molecule thereof a large number of aromatic rings (e.g., benzene rings or heterocyclic rings).

However, in general, an aromatic diamine derivative containing in the molecule thereof a large number of aromatic rings exhibits very poor solubility in a solvent. Such low solubility raises problems, including precipitation of diamine molecules in a solvent during the course of reaction, and limited reaction yield. For example, the following reaction:

An aromatic diamine derivative is known to be produced through a reaction pathway applying a raw material such as α-naphthylamine, β-naphthylamine, 4-aminodiphenyl, or benzidine, which compounds are known to exhibit mutagenicity. Production of these compounds, which are designated "specified chemical substances," is prohibited in Japan, and therefore demand has arisen for a production method which does not apply such a compound as a raw material or an intermediate.

For example, International Application PCT/JP02/02132 describes, as an example of such a production method, a method for producing an aromatic amine by reacting an aromatic amine having an arylalkyl group (e.g., a benzyl group) with an aromatic halide, without using a raw material or intermediate which may exhibit mutagenicity as described above.

However, difficulty is encountered in determining conditions for the aforementioned reaction, since the reaction requires a reduction reaction (e.g., hydrogenation) upon elimination of an arylalkyl group, which often causes reduction of an aromatic ring (i.e., a side reaction).

DISCLOSURE OF THE INVENTION

In order to solve the above-described problems, an object of the present invention is to provide a method for producing an aromatic diamine derivative which is useful as a charge transport material of an electrophotographic photoconductor or as an organic EL device material, and which can be produced at high yield in an efficient manner.

In order to achieve the aforementioned object, the present inventors have conducted extensive studies, and as a result have found that when an aromatic amide having a specific structure is reacted with an aromatic halide having a specific structure, an aromatic diamine derivative can be produced at high yield in an efficient manner. The present invention has been accomplished on the basis of this finding.

Accordingly, the present invention provides a method for producing an aromatic diamine derivative represented by the

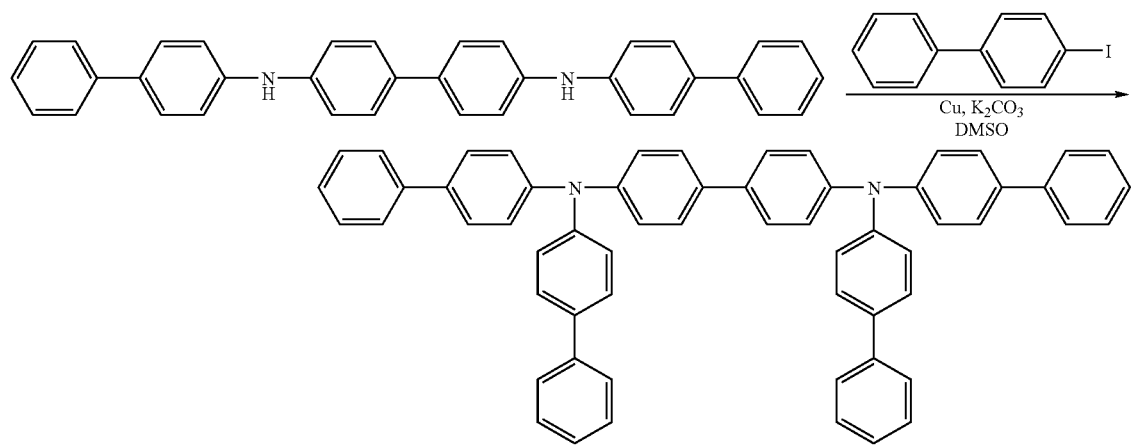

is difficult to progress, because of the presence of a large number of intramolecular aromatic rings, which cause the raw materials and reaction intermediates to exhibit low solubility.

following formula (3), which method comprises reacting an aromatic amide represented by the following formula (1) with an aromatic halide represented by the following formula (2):

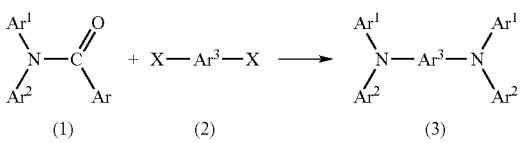

(wherein Ar represents a substituted or unsubstituted aryl group having 6 to 30 ring carbon atoms, or a substituted or unsubstituted heteroaryl group having 5 to 30 ring carbon atoms; each of $Ar^1$ and $Ar^2$ represents a substituted or unsubstituted aryl group having 6 to 30 ring carbon atoms, or a substituted or unsubstituted heteroaryl group having 5 to 30 ring carbon atoms; $Ar^3$ represents a substituted or unsubstituted arylene group having 6 to 30 ring carbon atoms, or a substituted or unsubstituted heteroarylene group having 5 to 30 ring carbon atoms; and X represents a halogen atom).

BEST MODE FOR CARRYING OUT THE INVENTION

The present invention will next be described in detail.

In the present invention, Ar represents a substituted or unsubstituted aryl group having 6 to 30 ring carbon atoms, or a substituted or unsubstituted heteroaryl group having 5 to 30 ring carbon atoms. Examples of the aryl group include a phenyl group, a biphenylyl group, a terphenylyl group, a naphthyl group, an anthranyl group, a phenanthryl group, a pyrenyl group, a chrysenyl group, and a fluoranthenyl group. Examples of the heteroaryl group include a pyrrolyl group, a furanyl group, a thiophenyl group, a triazole group, an oxadiazole group, a pyridyl group, and a pyrimidyl group. Of these, a phenyl group, a biphenylyl group, and a naphthyl group are particularly preferred.

In the present invention, each of $Ar^1$ and $Ar^2$ represents a substituted or unsubstituted aryl group having 6 to 30 ring carbon atoms, or a substituted or unsubstituted heteroaryl group having 5 to 30 ring carbon atoms. Examples of the aryl group include a phenyl group, a biphenylyl group, a terphenylyl group, a naphthyl group, an anthranyl group, a phenanthryl group, a pyrenyl group, a chrysenyl group, and a fluoranthenyl group. Examples of the heteroaryl group include a pyrrolyl group, a furanyl group, a thiophenyl group, a triazolyl group, an oxadiazolyl group, a pyridyl group, and a pyrimidyl group. Of these, a phenyl group, a biphenylyl group, and a naphthyl group are particularly preferred.

In the present invention, $Ar^3$ represents a substituted or unsubstituted arylene group having 6 to 30 ring carbon atoms, or a substituted or unsubstituted heteroarylene group having 5 to 30 ring carbon atoms. Examples of the arylene group include a phenylene group, a biphenylene group, a terphenylene group, a naphthylene group, an anthranylene group, a phenanthrylene group, a pyrenylene group, a chrysenylene group, and a fluoranthenylene group. Examples of the heteroarylene group include a pyrrolylene group, a furanylene group, a thiophenylene group, a triazolene group, an oxadiazolene group, a pyridylene group, and a pyrimidylene group. Of these, a phenylene group, a biphenylene group, and a naphthylene group are particularly preferred.

Examples of substituent(s) present in Ar and $Ar^1$ to $Ar^3$ include an aryl group having 5 to 30 ring carbon atoms, a C1-C12 alkyl or alkoxy group, and an amino group substituted by an aryl group having 5 to 30 ring carbon atoms.

Examples of the C1-C12 alkyl group include a methyl group, an ethyl group, an n-propyl group, an i-propyl group, an n-butyl group, an s-butyl group, a t-butyl group, an n-pentyl group, a cyclopentyl group, an n-hexyl group, a cyclohexyl group, and an adamantyl group.

Examples of the C1-C12 alkoxy group include a methoxy group, an ethoxy group, an n-propyloxy group, an i-propyloxy group, an n-butyloxy group, an s-butyloxy group, a t-butyloxy group, an n-pentyloxy group, a cyclopentyloxy group, an n-hexyloxy group, a cyclohexyloxy group, and an adamantyloxy group.

The number of substituent(s) present in each of $Ar^1$ to $Ar^3$ is preferably 0 to 4.

In the present invention, X represents a halogen atom. Examples of the halogen atom include iodine, bromine, chlorine, and fluorine, with iodine and bromine being particularly preferred.

The production method of the present invention is useful for the case where the total number of a benzene ring(s) and/or a heterocyclic ring(s) contained in an aromatic diamine derivative represented by formula (3) is 8 or more, particularly for the case where the total number is 10 or more.

In the production method of the present invention, preferably, an aromatic amide represented by formula (1) is reacted with an aromatic halide represented by formula (2) in the presence of a catalyst formed of a transition metal compound.

Examples of the transition metal include Mn, Fe, Co, Ni, Cu, Pd, Mo, Rh, Ru, V, Cr, Pt, Ir, and Zn. Among these, Ni, Pd, Pt, Zn, and Cu are preferred, with Cu being more preferred.

Examples of the form of the transition metal compound include fine powder of the transition metal, a halide of the transition metal, an oxide of the transition metal, and a chalcogenide compound of the transition metal, with a halide of the transition metal being preferred. Examples of the halide include a fluoride, a chloride, a bromide, and an iodide, with a bromide and an iodide being particularly preferred. A zero-valent or monovalent transition metal compound is preferably applied.

The amount of the catalyst to be added is generally 0.01 to 1 equivalent, preferably 0.1 to 0.5 equivalents, with respect to the aforementioned aromatic halide.

Preferably, reaction between the aromatic amide represented by formula (1) and the aromatic halide represented by formula (2) is carried out in the presence of a base. The base to be applied is preferably a hydroxide or salt of an alkali metal or alkaline earth metal. Among such hydroxides and salts, a hydroxide, a carbonate, a hydrogencarbonate, and an acetate are preferred, with a hydroxide, which is a strong base, being more preferred.

The amount of the base to be added is generally 2 to 5 equivalents, preferably 2 to 3 equivalents, with respect to the aforementioned aromatic halide.

The reaction solvent applied during the course of reaction between the aromatic amide represented by formula (1) and the aromatic halide represented by formula (2) is preferably a hydrocarbon compound, since this reaction requires high-temperature heating in the presence of a strong base. Particularly, a solvent having a high boiling point is preferably applied. Examples of the solvent which may be applied include xylene, decalin, dioxane, dimethylformamide (DMF), and dimethyl sulfoxide (DMSO), with xylene and decalin being preferred.

Before being applied, such a solvent is preferably subjected to dehydration or inert gas replacement. Dehydration or inert gas replacement of the solvent can be performed by means of a technique which is generally applied for organic synthesis. For example, a desiccant such as calcium chloride may be added to the solvent, or the solvent may be subjected to distillation in the presence of calcium hydride or metallic sodium under a stream of, for example, nitrogen or argon.

In the present invention, the temperature of the above-described reaction is generally room temperature to 150° C., preferably 100 to 150° C. The reaction time is 1 to 48 hours, preferably 6 to 18 hours. The reaction process (including preparation of a catalyst) is preferably carried out in an inert gas atmosphere.

Examples of the aromatic amide represented by formula (1), which is applied in the production method of the present invention, include N,N-di-(4-biphenylyl)benzamide, N-(1-naphthyl)-N-phenylbenzamide, N-(2-naphthyl)-N-phenylbenzamide, and N-(1-naphthyl)-N-(4-biphenylyl)benzamide.

Examples of the aromatic halide represented by formula (2), which is applied in the production method of the present invention, include 4,4'-diiodobiphenyl, 1,4-diiodobenzene, 4,4''-diiodo-p-terphenyl, 4,4'-dibromobiphenyl, 1,4-dibromobenzene, and 4,4''-dibromo-p-terphenyl.

Examples of the aromatic diamine derivative represented by formula (3), which is produced through the production method of the present invention, include N,N,N',N'-tetra(4-biphenylyl)benzidine and N,N'-di(1-naphthyl)-N,N'-diphenyl-4,4'-benzidine.

The aromatic diamine derivative produced through the production method of the present invention is useful as a charge transport material of an electrophotographic photoconductor or as an organic EL device material.

The present invention will next be described in more detail by way of Examples, which should not be construed as limiting the invention thereto.

EXAMPLE 1

Production of N,N,N',N'-tetra(4-biphenylyl) benzidine)

(1) Synthesis of N,N-di-(4-biphenylyl)benzamide

4-Bromobiphenyl (product of Tokyo Kasei Kogyo Co., Ltd.) (10.0 g), benzamide (product of Tokyo Kasei Kogyo Co., Ltd.) (2.31 g), cuprous iodide (product of Kanto Kagaku) (0.36 g), and anhydrous potassium carbonate (product of Kanto Kagaku) (5.8 g) were placed in a 100-mL three-neck flask. Subsequently, a stirrer piece was placed in the flask, a rubber cap (septum) was provided on each of the side necks of the flask, and a spiral reflux condenser was provided on the center neck. A three-way stop-cock and a balloon containing argon gas were provided on the reflux condenser. The atmosphere in the reaction system was replaced by the argon gas contained in the balloon by use of a vacuum pump (this procedure was performed three times).

Subsequently, diethylbenzene (50 mL) was added through the rubber septum by use of a syringe, the flask was placed in an oil bath, and the resultant mixture was gradually heated to 200° C. under stirring. Six hours later, the flask was removed from the oil bath, whereby the reaction was completed. Thereafter, the flask was allowed to stand in an argon atmosphere for 12 hours.

The resultant reaction mixture was transferred to a separatory funnel, and dichloromethane (100 mL) was added to the mixture, to thereby dissolve the precipitate in the mixture. After the mixture was washed with saturated brine (60 mL), the resultant organic layer was dried over anhydrous potassium carbonate. The potassium carbonate was separated through filtration, and the solvent of the resultant organic layer was removed through evaporation. Toluene (200 mL) and ethanol (40 mL) were added to the resultant residue, and the resultant mixture was heated to 80° C., with a drying tube being used, to thereby completely dissolve the residue in the mixture. Thereafter, the mixture was allowed to stand for 12 hours, and was gradually cooled to room temperature for recrystallization.

The thus-precipitated crystals were separated through filtration, and then dried under vacuum at 60° C., to thereby yield 7.22 g of N,N-di-(4-biphenylyl)benzamide.

(2) Synthesis of N,N,N',N'-tetra(4-biphenylyl)benzidine

The N,N-di-(4-biphenylyl)benzamide obtained above in (1) (1.00 g), 4,4'-diiodobiphenyl (product of Wako Pure Chemical Industries, Ltd.) (0.45 g), cuprous iodide (0.021 g), and potassium hydroxide (0.51 g) were placed in a 50-mL two-neck flask. Subsequently, a rubber cap (septum) was provided on the side neck, and a spiral reflux condenser was provided on the center neck. A three-way stop-cock and a balloon containing argon gas were provided on the reflux condenser. The atmosphere in the reaction system was replaced by the argon gas contained in the balloon by use of a vacuum pump (this procedure was performed three times).

Subsequently, xylene (20 mL) was added through the rubber septum by use of a syringe, the flask was placed in an oil bath, and the resultant mixture was gradually heated to 140° C. under stirring. After the mixture was stirred at 140° C. for six hours, the flask was removed from the oil bath, and was allowed to stand at room temperature for 12 hours.

The thus-precipitated product was completely dissolved in dichloromethane (50 mL), and the resultant solution was transferred to a separatory funnel. After the solution was washed with saturated brine (50 mL), the thus-separated organic layer was dried over anhydrous potassium carbonate. After filtration of the organic layer, the solvent was removed through evaporation, and toluene (150 mL) and ethanol (50 mL) were added to the resultant residue. The resultant mixture was heated to 80° C., with a drying tube being used, to thereby dissolve the precipitate in the mixture, followed by gradual cooling to room temperature. Subsequently, the resultant precipitate was separated through filtration, and washed with a small amount of toluene and ethanol. Thereafter, the precipitate was dried by use of a vacuum dryer at 60° C. for three hours, to thereby yield 0.72 g of N,N,N',N'-tetra(4-biphenylyl)benzidine.

The thus-obtained N,N,N',N'-tetra(4-iphenylyl)benzidine was subjected to measurement in terms of NMR (nuclear magnetic resonance spectrometry), FD-MS (field desorption mass spectrometry), and HPLC (high-performance liquid chromatography). The measurement results are as follows.

NMR: δ 90 MHz 7.1-7.8 (44H, m) FD-MS: 792, 396 HPLC: chemical purity of 99.6% or more The overall reaction yield was found to be 73%.

COMPARATIVE EXAMPLE 1

Production of N,N,N',N'-tetra(4-biphenylyl)benzidine: production through a pathway different from that of Example 1

(1) Synthesis of N,N-di-(4-biphenylyl)-benzylamine

4-Bromobiphenyl (product of Tokyo Kasei Kogyo Co., Ltd.) (10.0 g), sodium t-butoxide (product of Wako Pure Chemical Industries, Ltd.) (4.32 g), and palladium acetate (product of Wako Pure Chemical Industries, Ltd.) (42 mg) were placed in a 100-mL three-neck flask. Subsequently, a stirrer piece was placed in the flask, a rubber cap (septum) was provided on each of the side necks of the flask, and a spiral reflux condenser was provided on the center neck. A three-way stop-cock and a balloon, containing argon gas were provided on the reflux condenser. The atmosphere in the reaction system was replaced by the argon gas contained in the balloon by use of a vacuum pump (this procedure was performed three times).

Subsequently, dehydrated toluene (product of Wako Pure Chemical Industries, Ltd.) (60 mL), benzylamine (product of Tokyo Kasei Kogyo Co., Ltd.) (2.04 mL), and tris-t-butylphosphine (product of Aldrich, 2.22 mol/L toluene solution) (169 µL) were added through the rubber septum by use of a syringe, and the resultant mixture was stirred at room temperature for five minutes.

Subsequently, the flask was placed in an oil bath, and the resultant mixture was gradually heated to 120° C. under stirring. Seven hours later, the flask was removed from the oil bath, whereby the reaction was completed. Thereafter, the flask was allowed to stand in an argon atmosphere for 12 hours.

The resultant reaction mixture was transferred to a separatory funnel, and dichloromethane (300 mL) was added to the mixture, to thereby dissolve the precipitate in the mixture. After the mixture was washed with saturated brine (60 mL), the resultant organic layer was dried over anhydrous potassium carbonate. The potassium carbonate was separated through filtration, and the solvent of the resultant organic layer was removed through evaporation. Toluene (200 mL) and ethanol (40 mL) were added to the resultant residue, and the resultant mixture was heated to 80° C., with a drying tube being used, to thereby completely dissolve the residue in the mixture. Thereafter, the mixture was allowed to stand for 12 hours, and was gradually cooled to room temperature for recrystallization.

The thus-precipitated crystals were separated through filtration, and then dried under vacuum at 60° C., to thereby yield 6.73 g of N,N-di-(4-biphenylyl)-benzylamine.

(2) Synthesis of di-4-biphenylylamine

The N,N-di-(4-biphenylyl)-benzylamine obtained above in (1) (1.35 g) and palladium-activated carbon (product of Wako Pure Chemical Industries, Ltd., palladium content: 10 wt. %) (135 mg) were placed in a 300-mL one-neck flask, and chloroform (100 mL) and ethanol (20 mL) were added to the flask, followed by dissolution of these materials in the solvents.

Subsequently, a stirrer piece was placed in the flask, and then a three-way stop-cock equipped with a balloon filled with hydrogen gas (2 L) was provided on the flask. The atmosphere in the flask was replaced by the hydrogen gas by use of a vacuum pump (this procedure was performed 10 times). The balloon was filled with fresh hydrogen gas so as to compensate for the above-consumed hydrogen gas. After the hydrogen gas volume was returned to 2 L, the solution contained in the flask was vigorously stirred at room temperature for 30 hours. Thereafter, dichloromethane (100 mL) was added to the solution, and the catalyst was separated through filtration.

Subsequently, the resultant solution was transferred to a separatory funnel, and the solution was washed with a saturated aqueous solution of sodium hydrogencarbonate (50 mL). Thereafter, the resultant organic layer was separated, and dried over anhydrous potassium carbonate. After filtration of the organic layer, the solvent was removed through evaporation, and toluene (50 mL) was added to the resultant residue for recrystallization. The thus-precipitated crystals were separated through filtration, and then dried under vacuum at 50° C., to thereby yield 0.99 g of di-4-biphenylylamine.

(3) Synthesis of N,N,N',N'-tetra(4-biphenylyl)benzidine

The di-4-biphenylylamine obtained above in (2) (0.500 g), 4,4'-dibromobiphenyl (product of Tokyo Kasei Kogyo Co., Ltd.) (0.231 g), palladium acetate (0.0034 g), and sodium t-butoxide (0.157 g) were placed in a 50-mL two-neck flask. Subsequently, a rubber cap (septum) was provided on the side neck, and a spiral reflux condenser was provided on the center neck. A three-way stop-cock and a balloon containing argon gas were provided on the reflux condenser. The atmosphere in the reaction system was replaced by the argon gas contained in the balloon by use of a vacuum pump (this procedure was performed three times).

Subsequently, dehydrated toluene (10 mL) and tris-t-butylphosphine (product of Aldrich, 2.22 mol/L toluene solution) (13.4 µL) were added through the rubber septum by use of a syringe, the flask was placed in an oil bath, and the resultant mixture was gradually heated to 115° C. under stirring. After the mixture was stirred at 115° C. for six hours, the flask was removed from the oil bath, and was allowed to stand at room temperature for 12 hours.

The thus-precipitated product was completely dissolved in dichloromethane (500 mL), and the resultant solution was transferred to a separatory funnel. After the solution was washed with saturated brine (100 mL), the thus-separated organic layer was dried over anhydrous potassium carbonate. After filtration of the organic layer, the solvent was removed through evaporation, and toluene (150 mL) and ethanol (50 mL) were added to the resultant residue. The resultant mixture was heated to 80° C., with a drying tube being used, to thereby dissolve the precipitate in the mixture, followed by gradual cooling to room temperature. Subsequently, the resultant precipitate was separated through filtration, and washed with a small amount of toluene and ethanol. Thereafter, the precipitate was dried by use of a vacuum dryer at 60° C. for three hours, to thereby 0.453 g of yield N,N,N',N'-tetra(4-biphenylyl)benzidine.

The thus-obtained N,N,N',N'-tetra(4-biphenylyl) benzidine was subjected to measurement in terms of NMR, FD-MS, and HPLC. The measurement results are as follows.

NMR: δ 90 MHz 7.1-7.8 (44H, m) FD-MS: 792, 396 HPLC: chemical purity of 99.5% or more The overall reaction yield was found to be 63%.

COMPARATIVE EXAMPLE 2

Production of N,N,N',N'-tetra(4-biphenylyl)benzidine: the case where Ar of formula (1) is a methyl group (1) Synthesis of N,N-di-(4-biphenylyl)acetamide 4-Bromobiphenyl (product of Tokyo Kasei Kogyo Co., Ltd.) (10.0 g), sodium t-butoxide (product of Wako Pure Chemical Industries, Ltd.) (4.32 g), and palladium acetate (product of Wako Pure Chemical Industries, Ltd.) (42 mg) were placed in a 100-mL three-neck flask. Subsequently, a stirrer piece was placed in the flask, a rubber cap (septum) was provided on each of the side necks of the flask, and a spiral reflux condenser was provided on the center neck. A three-way stop-cock and a balloon containing argon gas were provided on the reflux condenser. The atmosphere in the reaction system was replaced by the argon gas contained in the balloon by use of a vacuum pump (this procedure was performed three times).

Subsequently, dehydrated toluene (product of Wako Pure Chemical Industries, Ltd.) (60 mL), acetamide (product of Tokyo Kasei Kogyo Co., Ltd.) (1.24 g), and tris-t-butylphosphine (product of Aldrich, 2.22 mol/L toluene solution) (169 μL) were added through the rubber septum by use of a syringe, and the resultant mixture was stirred at room temperature for five minutes.

Subsequently, the flask was placed in an oil bath, and the resultant mixture was gradually heated to 120° C. under stirring. Seven hours later, the flask was removed from the oil bath, whereby the reaction was completed. Thereafter, the flask was allowed to stand in an argon atmosphere for 12 hours.

The resultant reaction mixture was transferred to a separatory funnel, and dichloromethane (300 mL) was added to the mixture, to thereby dissolve the precipitate in the mixture. After the mixture was washed with saturated brine (60 mL), the resultant organic layer was dried over anhydrous potassium carbonate. The potassium carbonate was separated through filtration, and the solvent of the resultant organic layer was removed through evaporation. Toluene (200 mL) and ethanol (40 mL) were added to the resultant residue, and the resultant mixture was heated to 80° C., with a drying tube being used, to thereby completely dissolve the residue in the mixture. Thereafter, the mixture was allowed to stand for 12 hours, and was gradually cooled to room temperature for recrystallization.

The thus-precipitated crystals were separated through filtration, and then dried under vacuum at 60° C., to thereby yield 0.91 g of N,N-di-(4-biphenylyl)acetamide.

(2) Synthesis of N,N,N',N'-tetra(4-biphenylyl)benzidine

The procedure of Example 1 (2) was repeated, except that the N,N-di-(4-biphenylyl)benzamide (1.00 g) was replaced by the N,N-di-(4-biphenylyl)acetamide obtained above in (1) (0.85 g), to thereby yield 0.38 g of N,N,N',N'-tetra(4-biphenylyl)benzidine.

The thus-obtained N,N,N',N'-tetra(4-biphenylyl)benzidine was subjected to measurement in terms of NMR, FD-MS, and HPLC. The measurement results are as follows.

NMR: δ 90 MHz 7.1-7.8 (44H, m) FD-MS: 792, 396
HPLC: chemical purity of 99.3% or more
The overall reaction yield was found to be 5%.

INDUSTRIAL APPLICABILITY

As described above in detail, the method of the present invention can produce, at high yield in an efficient manner, an aromatic diamine derivative which is useful as a charge transport material of an electrophotographic photoconductor or as an organic electroluminescent device material.

The invention claimed is:

1. A method for producing an aromatic diamine derivative represented by formula (3), which method comprises reacting an aromatic amide represented by formula (1) with an aromatic halide represented by formula (2):

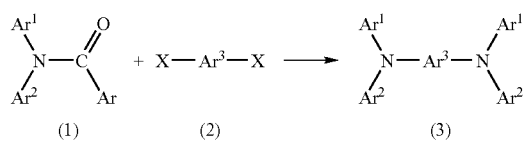

wherein Ar represents a substituted or unsubstituted aryl group having 6 to 30 ring carbon atoms, or a substituted or unsubstituted heteroaryl group having 5 to 30 ring carbon atoms; each of $Ar^1$ and $Ar^2$ represents a substituted or unsubstituted aryl group having 6 to 30 ring carbon atoms, or a substituted or unsubstituted heteroaryl group having 5 to 30 ring carbon atoms; $Ar^3$ represents a substituted or unsubstituted arylene group having 6 to 30 ring carbon atoms, or a substituted or unsubstituted heteroarylene group having 5 to 30 ring carbon atoms; and X represents a halogen atom.

2. A method for producing an aromatic diamine derivative as described in claim 1, wherein the aromatic diamine derivative represented by formula (3) contains a benzene ring(s) and/or a heterocyclic ring(s) in the total number of 8 or more.

3. A method for producing an aromatic diamine derivative as described in claim 1, wherein the aromatic amide represented by formula (1) is reacted with an aromatic halide represented by formula (2) in the presence of a catalyst composed of a transition metal compound.

4. A method for producing an aromatic diamine derivative as described in claim 3, wherein the transition metal compound is a copper compound.

5. A for producing an aromatic diamine derivative as described in claim 1, wherein the aromatic amide represented by formula (1) is reacted with an aromatic halide represented by formula (2) in the presence of a base composed of a hydroxide.

6. A method for producing an aromatic diamine derivative as described in claim 5, wherein the hydroxide is an alkali metal hydroxide and/or an alkaline earth metal hydroxide.

7. A method for producing an aromatic diamine derivative as described in claim 1, wherein reaction is performed in a hydrocarbon compound serving as a reaction solvent.

8. A method for producing an aromatic diamine derivative as described in claim 1, wherein the aromatic diamine compound serves as a charge transport material for use in an electrophotographic photoconductor.

9. A method for producing an aromatic diamine derivative as described in claim 1, wherein the aromatic diamine compound serves as an organic electroluminescent device material.

* * * * *